(12) United States Patent
Vacharathit

(10) Patent No.: US 8,907,165 B2
(45) Date of Patent: Dec. 9, 2014

(54) PRODUCTION OF PROVITAMIN A CAROTENOIDS IN MUSHROOMS AND USES THEREOF

(75) Inventor: Voranaddha Vacharathit, Cambridge, MA (US)

(73) Assignee: Medicine In Need Corporation, Cambridge, MA (US)

( * ) Notice: Subject to any disclaimer, the term of this patent is extended or adjusted under 35 U.S.C. 154(b) by 945 days.

(21) Appl. No.: 12/704,331

(22) Filed: Feb. 11, 2010

(65) Prior Publication Data
US 2010/0275329 A1    Oct. 28, 2010

Related U.S. Application Data

(60) Provisional application No. 61/214,197, filed on Apr. 22, 2009.

(51) Int. Cl.
| | |
|---|---|
| C12N 1/15 | (2006.01) |
| C12N 15/09 | (2006.01) |
| C12N 15/29 | (2006.01) |
| C12N 15/31 | (2006.01) |
| C12N 15/52 | (2006.01) |
| A01G 1/04 | (2006.01) |
| C12N 15/82 | (2006.01) |
| C12N 15/80 | (2006.01) |

(52) U.S. Cl.
CPC .......... *C12N 15/80* (2013.01); *C12N 15/8243* (2013.01)
USPC .......................................... 800/297; 435/171

(58) Field of Classification Search
None
See application file for complete search history.

(56) References Cited

U.S. PATENT DOCUMENTS 8,557,585 B2 *  10/2013  Ha et al. .................. 435/468

FOREIGN PATENT DOCUMENTS

| WO | 9502691 | 1/1995 |
| WO | 9845455 | 10/1998 |
| WO | 2004039985 | 5/2004 |
| WO | 2004063358 | 7/2004 |
| WO | 2007042304 | 4/2007 |
| WO | 2009028903 | 3/2009 |

OTHER PUBLICATIONS

Chen, X. et al. Applied Environmental Microbiology, Oct. 2000; pp. 4510-4513.*
Barros, L. et al. Food Chemistry, vol. 111, pp. 61-66.*
Verwall et al. Applied and Environmental Microbiology, Jul. 2007 p. 4342-4350.*
Alves, et al., "Highly Efficient Production of Laccase by the Basidiomycete *Pycnoporus cinnabarinus*", App. Env. Microbiol., 70:6379-6384 (2004).
Armstrong, "Genetics of eubacterial carotenoid biosynthesis: a colorful tale.", Annu. Rev. Microbiol., 51:629-659 (1997).
Arrach, et al., "Mutants of the carotene cyclase domain of al-2 from *Neurospora crassa*." , Mol. Genet. Genomics, 266(6):914-921 (2002).
Arrach, "A single gene for lycopene cyclase, phytoene synthase, and regulation of carotene biosynthesis in Phycomyces." , Proc. Natl. Acad. Sci. U.S.A., 98 (4):1687-1692 (2001).
Block, et al., "Engineering herbicide resistance in plants by expression of a detoxifying enzyme." , EMBO J., 6:2513-2518 (1987).
Bretagne-Sagnard, et al., "Selection of transgenic flax plants is facilitated by spectinomycin", Transgenic Res., 5:131-137 (1996).
Chamovitz, et al., "Molecular cloning and expression in *Escherichia coli* of a cyanobacterial gene coding for phytoene synthase, a carotenoid biosynthesis enzyme" , FEBS Lett., 296(3):305-310 (1992).
Chen, et al., "A Fruiting Body Tissue Method for Efficient Agrobacterium-Mediated Transformation of *Agaricus bisporus*", App. Env. Microbiol., 66:4510-4513 (2000).
Godio, et al., "Agrobacterium tumefaciens-mediated transformation of the antitumor clavaric acid-producing basidiomycete *Hypholoma sublateritium*", Curr. Genet., 46:287-294 (2004).
Gouka, et al., "Transformation of *Aspergillus awamori* by Agrobacterium tumefaciens-mediated homologous recombination", Nat. Biotechnol., 17 (6):598-601 (1999).
Harmsen, et al., "Sequence analysis of the glyceraldehyde-3-phosphate dehydrogenase genes from the basidiomycetes Schizophyllum commune, *Phanerochaete chrysosporium* and *Agaricus bisporus*"., Current Genetics, 22:447-454 (1992).
Hausmann and Sandman, "A single five-step desaturase is involved in the carotenoid biosynthesis pathway to beta-carotene and torulene in *Neurospora crassa*", Fungal Genet. Biol., 30:147-153 (2000).
Krubasik and Sandmann, "A carotenogenic gene cluster from Brevibacterium linens with novel lycopene cyclase genes involved in the synthesis of aromatic carotenoids.", Mol. Gen. Genet., 263:423-432 (2000).
Mikosch, et al., "Transformation of the cultivated mushroom *Agaricus bisporus*(Lange) using T-DNA from *Agrobacterium tumefaciens*", Curr. Genet., 39 (1):35-39 (2001).
Naik, et al., "Genetic manipulation of carotenoid pathway in higher plants", Current Science, Indian Academy of Sciences, 85(10):1423-1430 (2003).
Rodríguez-Sáiz, et al., "*Blakeslea trispora* Genes for Carotene Biosynthesis", Appl. Env. Microbiol., 70:5589-5594 (2004).
Schneeman, "Linking agricultural production and human nutrition", Journal of the Science of Food and Agriculture, 81(1):3-9 (2001).
Schuren and Wessels, "Expression of heterologous genes in *Schizophyllum commune* is often hampered by the formation of truncated transcripts.", Curr. Genet., 33(2):151-156 (1998).

(Continued)

*Primary Examiner* — Russell Kallis
(74) *Attorney, Agent, or Firm* — Pabst Patent Group LLP

(57) ABSTRACT

Mushrooms genetically engineered to produce provitamin A carotenoids including α-carotene, β-carotene, γ-carotene, and β-cryptoxanthin are provided. In some embodiments, mushrooms are transformed with genes that encode enzymes that have phytoene synthase, pyhtoene dehydrogenase and lycopene cyclase activities and function to convert GGPP to one or more provitamin A carotenoids. Mushrooms are transformed using known methods, including *Agrobacterium*-mediated transformation. Transgenic mushrooms producing provitamin A carotenoids are useful to treat, alleviate, reduce, and/or inhibit one or more symptoms of a disease or disorder associated with vitamin A deficiency (VAD).

25 Claims, 1 Drawing Sheet

(56) References Cited

OTHER PUBLICATIONS

Schuurs, et al., "Homology-dependent silencing of the SC3 gene in *Schizophyllum commune*.", Genetics, 147(2):589-596 (1997).

Schwender, et al., "Biosynthesis of isoprenoids (carotenoids, sterols, prenyl side-chains of chlorophylls and plastoquinone) via a novel pyruvate/glyceraldehyde 3-phosphate non-mevalonate pathway in the green alga *Scenedesmus obliquus*", Biochem., 316:73-80 (1996).

Steinbrenner and Linden, "Regulation of two carotenoid biosynthesis genes coding for phytoene synthase and carotenoid hydroxylase during stress-induced astaxanthin formation in the green alga *Haematococcus pluvialis*.", Plant Physiol., 125(2):810-817 (2001).

Strobel, et al., "Carotenoids and carotenogenic genes in *Podospora anserina*: engineering of the carotenoid composition extends the life span of the mycelium", Current Genetics, 55(2):175-184 (2009).

Van Der Rhee, et al., "Highly efficient homologous integration via tandem exo-beta-1, 3-glucanase genes in the common mushroom, *Agaricus bisporus*", Curr. Genet., 30(2)1 66-173 (1996).

Van Der Rhee, et al., "Transformation of the cultivated mushroom, *Agaricus bisporus*, to hygromycin B resistance.", Mol. Gen. Genet., 250(3):252-258 (1996).

Velayos, et al., "A bifunctional enzyme with lycopene cyclase and phytoene synthase activities is encoded by the carRP gene of *Mucor circinelloides*", Eur. J. Biochem., 267 (17):5509-5519 (2000).

Verdoes, et al., "Isolation and functional characterisation of a novel type of carotenoid biosynthetic gene from *Xanthophyllomyces dendrorhous*", Mol. Gen. Genet., 262(3):453-461 (1999).

Verdoes, et al., "Metabolic engineering of the carotenoid biosynthetic pathway in the yeast *Xanthophyllomyces dendrorhous* (*Phaffia rhodozyma*)", Applied and Environmental Microbiology, 69(7):3728-3738 (2003).

Verwaal, et al., "High-level production of beta-carotene in *Saccharomyces cerevisiae* by successive transformation with carotenogenic genes from *Xanthophyllomyces dendrorhous*", Applied and Environmental Microbiology, 73(13):4342-4350 (2007).

* cited by examiner

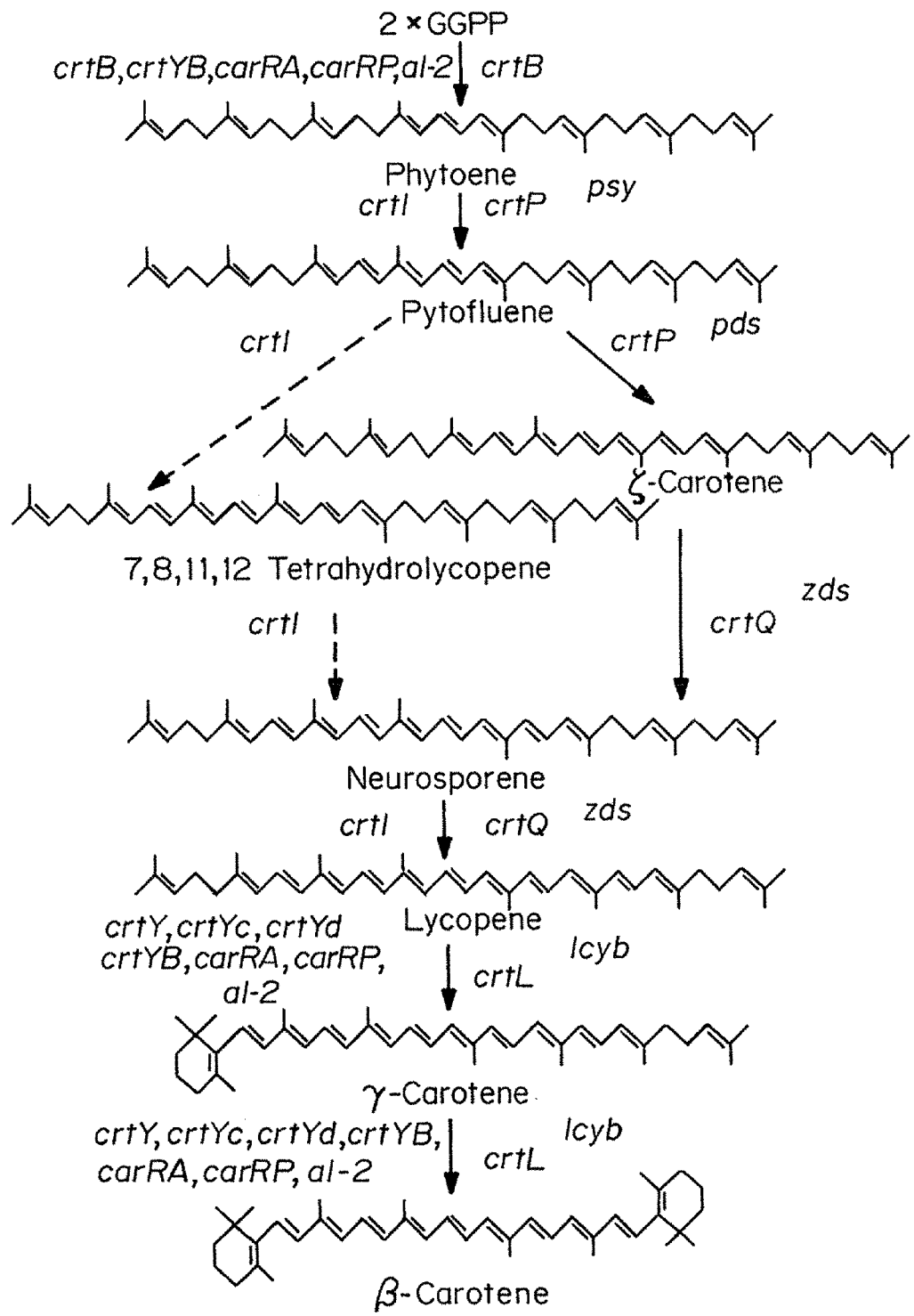

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Concensus Sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid

<400> SEQUENCE: 1

Asp Xaa Xaa Xaa Xaa Gly Xaa Gly Xaa Ala Xaa Xaa Xaa Xaa Ala
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Concensus Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
```

```
<222> LOCATION: (9)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 2

Phe Xaa Tyr Xaa Xaa Xaa Xaa Ser Xaa Xaa Xaa Xaa Xaa Xaa Glu Xaa
1               5                   10                  15

Thr

<210> SEQ ID NO 3
<211> LENGTH: 13
<212> TYPE: PRT
<213> ORGANISM: Artificial Sequence
<220> FEATURE:
<223> OTHER INFORMATION: Concensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 3

Gly Xaa Xaa Ala Xaa Xaa Xaa His Pro Xaa Xaa Gly Tyr
1               5                   10
```

PRODUCTION OF PROVITAMIN A CAROTENOIDS IN MUSHROOMS AND USES THEREOF

CROSS REFERENCE TO RELATED APPLICATIONS

This application claims priority to and benefit of U.S. Provisional Patent Application No. 61/214,197 filed on Apr. 22, 2009, and where permissible is incorporated by reference in its entirety.

FIELD OF THE INVENTION

This invention is generally related to agricultural biotechnology, in particular to mushrooms that produce provitamin A carotenoids.

BACKGROUND OF THE INVENTION

Humans require at least 49 nutrients to meet their metabolic needs. Inadequate consumption of even one of these nutrients will result in adverse metabolic disturbances leading to sickness, poor health, impaired development in children, and large economic costs to society (Branca and Ferrari, *Annals of Nutrition and Metabolism,* 46:8-17 (2002); Golden, *Acta Paediatrica Scandinavica,* 374:95-110 (1991); Ramakrishnan, et al., *Nutrition Research,* 19: 103-159 (1999)). Importantly, the primary source of all nutrients for people comes from agricultural products. If agricultural systems fail to provide enough products containing adequate quantities of all nutrients during all seasons, dysfunctional food systems result that cannot support healthy lives. Unfortunately, this is the case for many agricultural systems in many developing nations in the Global South (Graham, et al., *Advances in Agronomy,* 70:77-142 (2001); Schneeman, *Journal of the Science of Food and Agriculture,* 81:3-9 (2001)).

Nearly two-thirds of all deaths of children are associated with nutritional deficiencies, many from micronutrient deficiencies (Caballero, *Annals of Nutrition and Metabolism,* 46:3-7 (2002)). Marginal intakes of micronutrients have been shown to contribute to increased morbidity and mortality rates, diminished livelihoods, and adverse effects on learning ability, development, and growth in infants and children. Much of childhood stunting has been attributed to the impact of micronutrient deficiencies on children from early fetal stages of development through the fourth year of life (Branca and Ferrari, *Annals of Nutrition and Metabolism,* 46:8-17 (2002)). By any measure, micronutrient malnutrition is currently of alarming proportions in many developing nations.

Vitamin A, a necessary micronutrient obtained from diet in the form of provitamin A, is important to the human immune and visual systems. Its deficiency leads to the death of 1 million children annually, as well as to eye damage and blindness in 1.3 million children in Africa alone. Estimates by the World Health Organization place 100 to 140 million children as high risk for vitamin A deficiency, and 4 million as having severe vitamin A deficiency. Vitamin A deficiency may increase the risk of maternal mortality in pregnant women. Nearly 600,000 women die from childbirth-related causes each year, the vast majority of them from complications which could be reduced through better nutrition, such as vitamin A.

Current attempts to eradicate vitamin A deficiency in the most needy populations in South Asia and Sub-Saharan Africa focus on supplement distribution. This is a partnership between the local government, NGOs, and even the private sector to set up the appropriate infrastructure and resources for the distribution of vitamin A supplements on what is most commonly a quarterly or biannual basis (The United Nations Children's Fund, http://www.childinfo.org/vitamina.html, Nov. 11, 2008). However, these programs, while alleviating suffering and deprivation in many areas, succumb to a common pitfall: none allow for self-sustenance of the population at risk, instead inadvertently promoting their reliance on the distributors. Furthermore, consistent distribution of supplements requires the deployment of manpower from the local government on a frequent basis, which inevitably increases costs, thereby making these programs less effective.

Several alternatives have relatively recently been proposed to address the problem of non-self-sufficiency. These include the genetically modified "Golden Rice"—rice engineered to overproduce beta-carotene (provitamin A), and programs to promote the planting of sweet potatoes, which is a good vitamin A source. However, both of these solutions come with their own problems. Both require tending of crops, which necessitates vast resources in the form of land, manpower, and water. Also, in both cases, the edible parts are small compared to the whole plant, which is useless after harvest, and the regeneration time of a new plant generation is long (months). Further, yields depend on climate conditions and are not readily controllable. Most importantly, however, is the fact that planting these crops in the hopes of obtaining a sustained vitamin A source often precludes the planting of other plant species for commercial purposes. People cannot plant other things to be sold to the local market because their land has been used to grow rice or sweet potatoes. In light of these deficiencies, a new foodstuff that can serve as a more efficient source of provitamin A is highly desirable.

Therefore, it is an object of the invention to provide alternative renewable food sources of provitamin A that have a fast generation time, grow in a wide variety of conditions, and use less land, water and manpower to grow than most commercial crops.

It is another object of the present invention to provide more efficient and less expensive methods for preventing vitamin A deficiency and diseases and disorders associated therewith.

SUMMARY OF THE INVENTION

Mushrooms have been genetically engineered to produce provitamin A carotenoids. This provides an inexpensive method for increasing vitamin A levels in individuals at risk for or with one or more symptoms associated with vitamin A deficiency (VAD). Any suitable mushroom can be genetically engineered for production of provitamin A carotenoids. In preferred embodiments, the mushrooms are edible varieties of mushroom, including, but not limited to, mushrooms that belong to the order of Agaricales within the subdivision of Basidiomycetes.

The transgenic mushrooms are engineered to produce one or more provitamin A carotenoids, such as α-carotene, β-carotene, γ-carotene, and the xanthophyll β-cryptoxanthin. The upper isoprenoid pathway, which produces geranylgeranyl pyrophosphate as a metabolite, is common to both carotenogenic and non-carotenogenic organisms. In some embodiments, mushrooms are transformed with genes that encode enzymes that convert geranylgeranyl pyrophosphate (GGPP) to one or more provitamin A carotenoids. In a preferred embodiment, the carotenoid is β-carotene. In other embodiments, mushrooms that produce farnesyl pyrophosphate (FPP) as a final metabolite of the upper isoprenoid pathway are further transformed with a gene that codes for a GGPP synthetase.

Genes which may be used to transform mushrooms to convert GGPP to one or more provitamin A carotenoids include genes that encode enzymes that have phytoene synthase, pyhtoene dehydrogenase and lycopene cyclase activities. Suitable genes are known in the art or may be derived from any suitable source, including, but not limited to, carotenogenic non-photosynthetic prokaryotes (bacteria), carotenogenic photosynthetic prokaryotes or eukaryotes (i.e., cyanobacteria, algae and plants), or carotenogenic non-photosynthetic eukaryotes (i.e., archeae and fungi), or a combination thereof. Preferably the genes are codon optimized for expression or over-expression in mushrooms. Codon optimization can be used as a mechanism to fine-tune the ultimate concentration of the desired carotenoid in the final product. Mushrooms can additionally be transformed with one or more genes that confer a desirable trait, such as increased fatty acid synthesis or increased resistance to pests, such as flies, or increased resistance to drought.

In some embodiments, genes are transformed into mushrooms using vectors containing an expression cassette that includes the coding sequence of the gene operably linked to a promoter suitable to drive expression of the gene in mushrooms. Suitable promoters include, but are not limited to, constitutive promoters, inducible promoters and tissue-specific or developmentally regulated promoters. Vectors for transformation of mushrooms preferably also contain transcription terminators and optionally one or more reporter or selectable marker genes.

Mushrooms can be transformed using any suitable method known in the art, including, but not limited to, transformation of naked DNA with or without a carrier, electroporation, particle bombardment, and *Agrobacterium*-mediated transformation. In preferred embodiments, mushrooms are transformed using *Agrobacterium*-mediated transformation. Any suitable cells or tissues of mushrooms can be used as host cells for transformation, including, but not limited to, protoplasts, spores, vegetative mycelium and fruit body tissue. Transformed mushroom cells expressing the transgenes can then be selected and grown into mushrooms in accordance with conventional techniques.

Transgenic mushrooms producing provitamin A carotenoids can be administered or ingested by individuals in an effective amount to treat, alleviate, reduce, and/or inhibit one or more symptoms of a disease or disorder associated with vitamin A deficiency (VAD), including, but not limited to, blindness, abnormal visual adaptation to darkness (nyctalopia), dry skin, dry hair, broken fingernails, impairment of the humoral and cell-mediated immune system, bitot spots, pruritus, keratomalacia, xerophthalmia, corneal perforation, follicular hyperkeratosis (phrynoderma), excessive deposition of periosteal bone, anemia, and keratinization of mucous membranes. Provitamin A carotenoids can be obtained from edible mushrooms by ingestion of all or a part of the transgenic mushroom, including the fruiting body. Alternatively, provitamin A can be harvested from the transgenic mushrooms.

BRIEF DESCRIPTION OF THE DRAWINGS

FIG. 1 is a schematic showing biosynthetic pathways for the conversion of geranylgeranyl pyrophosphate to β-carotene and the genes required at each step. Genes from non-photosynthetic organisms are shown on the left side of the schematic, and genes from photosynthetic organisms are shown on the right side of the schematic.

DETAILED DESCRIPTION OF THE INVENTION

I. Definitions

As used herein, the tend "provitamin A carotenoids" refers to carotenoids that can be converted in the human body to retinal. Provitamin A carotenoids include the carotenes, α-carotene, β-carotene, γ-carotene, and the xanthophyll, β-cryptoxanthin.

As used herein, the term "mushroom" refers to any large fungus that develops a visible fruiting body, in contrast to filamentous fungi. Mushrooms are usually of the phyla Basidiomycetes; especially one of the subphyla Agaricales. Unless otherwise specified, the term "mushroom" refers to edible varieties of mushrooms.

As used herein, the terms "mushroom tissue" or "mushroom part" refers to a plurality of mushroom cells that are largely differentiated into a structure that is present at any stage of a mushroom's development. Such structures include, but are not limited to, a fruit body tissue, protoplasts, spores, or vegetative mycelium.

As used herein the term "*Agrobacterium*" includes any bacterial species and its conservatively modified variants that is capable of infecting a desired fungal cell, such as a *Agrobacterium tumefaciens* Ti plasmid.

As used herein, the term "encoding" or "encoded", with respect to a specified nucleic acid, means that the specified nucleic acid contains the information for translation into a specified protein. A nucleic acid encoding a protein may contain non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

As used herein, the term "expression" refers to biosynthesis of a gene product. Structural gene expression involves transcription of the structural gene into RNA, which is modified to mRNA, and then translation of the mRNA into one or more polypeptides.

As used herein, a "vector" is a replicon, such as a plasmid, phage, or cosmid, into which another DNA segment may be inserted to replicate the inserted segment.

As used herein, an "expression vector" is a vector that includes one or more expression control sequences.

As used herein, an "expression control sequence" is a DNA sequence that controls and regulates the transcription and/or translation of another DNA sequence.

As used herein, terms "promoter", "promoter region", or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease SI), as well as protein binding domains (consensus sequences) responsible for the binding of RNA polymerase. The term "promoter" includes the essential regulatory features of said sequence and may optionally include a long terminal repeat region prior to the translation start site.

As used herein, "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

As used herein the term "heterologous" means from another host. The other host can be the same or different species.

As used herein, "transgenic" refers to an organism in which a nucleic acid fragment containing a heterologous nucleotide sequence has been introduced. The transgenes in the transgenic organism are preferably stable and inheritable.

The term "non-transgenic mushroom" refers to a mushroom that has not been genetically engineered, i.e., transformed with a nucleic acid sequence from another host. A "corresponding non-transgenic mushroom" refers to the mushroom prior to the introduction of heterologous nucleic acids that encode enzymes for producing provitamin A carotenoids.

As used herein, the term "conservatively modified variant" refers to substitutions, deletions, or additions to a nucleic acid, peptide, polypeptide, or protein sequence which alters, adds, or deletes a single amino acid or a small percentage of amino acids in the encoded sequence, typically where the alteration results in the substitution of one or more amino acids with a chemically similar amino acid. Conservative substitution tables providing functionally similar amino acids are well known in the art. Conservatively modified variants typically provide similar biological activity as the unmodified polypeptide sequence from which they are derived. For example, substrate specificity or enzyme activity is generally at least 30%, 40%, 50%, 60%, 70%, 80%, or 90% of the native protein for its native substrate. As used herein, the term "phytoene synthase activity" refers to enzymatic activities that convert geranylgeranyl pyrophosphate (GGPP) to phytoene.

As used herein, the term "phytoene dehydrogenase activity" refers to enzymatic activities that convert phytoene to lycopene. Phytoene conversion to lycopene may involve one or more intermediates, including $\zeta$-carotene. The term "phytoene dehydrogenase activity" encompasses $\zeta$-carotene dehydrogenase activity.

As used herein, the term "lycopene cyclase activity" refers to enzymatic activities that convert lycopene to $\beta$-carotene. Lycoene conversion to $\beta$-carotene may involve one or more intermediates.

II. Transgenic Mushrooms Producing Provitamin A Carotenoids

Mushrooms are genetically engineered to produce provitamin A carotenoids. The mushrooms are transformed with heterologous genes that encode enzymes in provitamin A carotenoid biosynthetic pathways to produce provitamin A carotenoids from endogenous provitamin A precursors in mushrooms.

A. Mushroom Hosts for Provitamin A Carotenoid Production

Fungi are microscopic, spore-bearing organisms that lack chlorophyll and therefore derive nourishment from dead or living organic matter. Because they share characteristics of both plants and animals, they are classified separately in the kingdom Fungi (Eumycota). Within this kingdom, there are the "filamentous fungi", so named because their vegetative bodies consist of small thread-like filaments referred to as "hyphae". Typically, the hyphae grow in a branching fashion, spreading over or within the substrate used as a source of nourishment, thereby forming a network of hyphae called "mycelium". Thus, the mycelium is the vegetative body of the fungus. In the life cycle of most filamentous fungi, the vegetative mycelium gives rise to either asexual or sexual spores. Asexual spores are referred to by a variety of names, but commonly used terms are "conidia", "condiospores", or simply "spores". The vegetative mycelium of the fungus may differentiate, with the appropriate biological and environmental cues, into a sexual reproductive spore-bearing structure. Some fungi produce sizable, fibrous ("fleshy"), spore-bearing reproductive structures variously called "mushrooms", "fruit bodies", "basidiocarps", "ascocarps", "conks", or "basidomes". The fruit bodies of some fungi are edible; being valued for their culinary, nutritional, or medicinal qualities, and, as such, are highly sought after or grown commercially.

The fruit body may be differentiated into specialized tissues such as the fleshy umbrella-shaped cap (pileus), stem (stipe), cup at the base of the stem (volva), and gills (lamallae) bearing the sexual spores. A thin tissue known as the veil (velium) may cover the underside of the cap. The veil ruptures as the fruit body approaches maturity, exposing the gills and permitting the discharge of the sexual spores into the environment. However, the fruit bodies of some fungi lack gills all together, and instead are composed of fleshy tissue perforated with small pores or locules bearing the sexual spores. Sexual spores produced by the fleshy reproductive structures of fungi are described by numerous terms, as for example, "ascospores", "basidiospores", or simply "spores".

The fruit body of fungi is functionally comparable to the reproductive structure of plants known as the flower, whereas both asexual and sexual spores are comparable to the seed of plants, being important in the dispersal and survival of the fungus in nature. Under suitable environmental conditions, the spore germinates to form another generation of vegetative hyphae and so completing the life cycle of the fungus.

The major phyla of fungi have been classified mainly on the basis of characteristics of their sexual reproductive structures. Currently, seven phyla are proposed: Microsporidia, Chytridiomycota, Blastocladiomycota, Neocallimastigomycota, Glomeromycota, Ascomycota, and Basidiomycota. The Ascomycota, and Basidiomycota are contained within a branch of the Eumycota representing subkingdom Dikarya.

The Ascomycota, commonly known as sac fungi or ascomycetes, constitute the largest taxonomic group within the Eumycota. These fungi form meiotic spores called ascospores, which are enclosed in a special sac-like structure called an asccus. This phylum includes morels, a few mushrooms and truffles, single-celled yeasts (e.g., of the genera *Saccharomyces, Kluyveromycees, Pichia*, and *Candida*), and many filamentous fungi living as saprotrophs, parasites, and mutualistic symbionts.

Most common mushrooms are members of the Basidiomycota. In addition to mushrooms, the Basidiomycota, or basidiomycetes, include puffballs, stinkhorns, bracket fungi, other polypores, jelly fungi, boletes, chanterelles, earth stars, smuts, bunts, rusts, mirror yeasts, and the human pathogenic yeast, *Cryptococcus*. Basidiomycetes are filamentous fungi composed of hyphae (except for those forming yeasts), and reproducing sexually via the formation of specialized club-shaped end cells called basidia that normally bear external basidiospores.

Any suitable mushroom can serve as a host for production of provitamin A carotenoids. In preferred embodiments, the mushroom is an edible mushroom. Many edible mushrooms belong to the order of Agaricales within the subdivision of Basidiomycetes. The family of Agaricaceae is large and includes many familiar mushrooms. For instance, *Agaricus bisporus* is the common cultivated white button mushroom. *Pleurotus ostreatus*, belonging to the family of Pleurotaceae, is a commercially important edible mushroom commonly known as the oyster mushroom. This fungus is industrially produced as human food, and it accounts for nearly a quarter of the world mushroom production. In one embodiment, a *Pleurotus* spp. or *Auricularia* spp. is used as a host to transform with expression vectors containing genes that encode enzymes in provitamin A carotenoid biosynthetic pathways. Members of other families within the subclass of holobasidiomycetida (substantial mushrooms) can also be used, such as Schizophyllacea.

In one embodiment, the mushroom is a Basidiomycete host for provitamin A carotenoid biosynthesis prefereably selected from the group consisting of *Agaricus arvensis, Agaricus bisporus, Agaricus blazei, Agrocybe aegerita, Coprinus cinereus, Lentinus edodes, Lepista nuda, Pleurotus ostreatus, Phanerochaete chrysosporium, Schizophyllum commune, Hypsizygus tessulatus, Pholiota nameko, Boletus edulis, Flammulina velutipes, Hericium erinacelus, Volvariella volvacea, Grifola frondosa, Ganoderma lucidum, Tremella fuciformis, Auricularia auricular, Lyophyllum descastes, Naematoloma sublaterium, Stropharia rugoso-annulata* and *Cordyceps sinense*. In a preferred embodiment, the basidiomycete is *Pleurotus ostreatus*.

B. Genes for Producing Provitamin A Carotenoids

The mushrooms are transformed with the genes encoding one or more enzymes in the carotenoid synthetic pathway using vectors. The vectors can be vectors used for transient expression of the genes or vectors used to incorporate the heterologous nucleic acids into the genome of the mushroom. The choice of particular bacterial vector involves no more than routine optimization of parameters by those of skill in the art. Other bacteria may be used and are available to those of skill in the art through sources such as Genbank. Thus, in certain embodiments the transgenic mushrooms express one or more heterologous genes epigenomicly or genomicly.

1. Provitamin A Carotenoids

Carotenoids represent one of the most widely distributed and structurally diverse classes of natural pigments, producing pigment colors of light yellow to orange to deep red. Carotenoids are synthesized by all photosynthetic organisms, as well as some bacteria and fungi, not including mushrooms. These pigments have important functions in photosynthesis, nutrition, and protection against photooxidative damage. Animals do not have the ability to synthesize carotenoids but must obtain these nutritionally important compounds through their dietary sources.

There are over 600 known carotenoids that are split into two classes; xanthophylls (which contain oxygen) and carotenes (which are purely hydrocarbons, and contain no oxygen). Carotenoids in general absorb blue light. They serve two key roles in plants and algae: they absorb light energy for use in photosynthesis, and they protect chlorophyll from photodamage. In humans, some carotenoids are important as metabolic precursors for vitamin A.

Vitamin A is needed by the retina of the eye in the form of the light-absorbing molecule retinal. This molecule is required for both scotopic and color vision. Vitamin A also functions in a very different role, as an irreversibly oxidized form retinoic acid, which is an important hormone-like growth factor for epithelial and other cells. In foods of animal origin, the major form of vitamin A is an ester, primarily retinyl palmitate, which is converted to an alcohol (retinol) in the small intestine. The retinol form functions as a storage form of vitamin A, and can be converted to and from its visually active aldehyde form, retinal. The associated acid (retinoic acid), a metabolite which can be irreversibly synthesized from vitamin A, has only partial vitamin A activity, and does not function in the retina or some essential parts of the reproductive system.

Retinol, the form of vitamin A absorbed when eating animal food sources, is a yellow, fat-soluble substance. Since the pure alcohol form is unstable, the vitamin is found in tissues in a form of retinyl ester. In herbivores and omnivore animals, including humans, four carotenoids (β-carotene, α-carotene, γ-carotene, and β-cryptoxanthin) have vitamin A activity, meaning they can be converted by enzymes in the body to retinal. These carotenoids are referred to as provitamin A carotenoids. All forms of vitamin A have a β-ionone ring to which an isoprenoid chain is attached, called a retinyl group. This structure is essential for vitamin activity. β-carotene can be represented as two connected retinyl groups, which are used in the body to contribute to vitamin A levels. α-carotene and γ-carotene also have a single retinyl group, which give them some vitamin A activity. β-cryptoxanthin possesses an ionone group and has vitamin A activity in humans. None of the other carotenes have vitamin A activity.

2. Carotenoid Metabolic Pathways

Structurally, most common carotenoids are 40-carbon ($C_{40}$) terpenoids; however, carotenoids with only 30 carbon atoms ($C_{30}$; diapocarotenoids) are detected in some species. Biosynthesis of each of these types of carotenoids is derived from the isoprene biosynthetic pathway and its five-carbon universal isoprene building block, isopentenyl pyrophosphate (IPP). This biosynthetic pathway can be divided into two portions: 1) the upper isoprene pathway, which leads to the formation of geranylgeranyl pyrophosphate (GGPP); and 2) the lower carotenoid biosynthetic pathway, which convert GGPP into long $C_{30}$ and $C_{40}$ carotenogenic compounds, including provitamin A carotenoids.

a. The Upper Isoprenoid Pathway

Isoprenoid biosynthesis occurs through either of two pathways, generating the common $C_5$ isoprene subunit, isopentenyl pyrophosphate (IPP). First, IPP may be synthesized through the well-known acetate/mevalonate pathway. However, studies have demonstrated that the mevalonate-dependent pathway does not operate in all living organisms. An alternate mevalonate-independent pathway for IPP biosynthesis has been characterized in bacteria and in green algae and higher plants (Horbach, et al., *FEMS Microbiol. Lett.,* 111:135-140 (1993); Rohmer, et al., *Biochem.,* 295:517-524 (1993); Schwender, et al., *Biochem.,* 316:73-80 (1996); Eisenreich, et al., *Proc. Natl. Acad. Sci. USA,* 93:6431-6436 (1996)).

IPP may be isomerized to dimethylallyl pyrophosphate (DMAPP) via isopentenyl diphosphate isomerase (or "IPP isomerase"). The synthesis of FPP occurs via the isomerization of IPP to dimethylallyl pyrophosphate (DMAPP). This reaction is followed by a sequence of three prenyltransferase reactions leading to the creation of geranyl pyrophosphate (GPP; a 10-carbon molecule), farnesyl pyrophosphate (FPP; a 15-carbon molecule), and geranylgeranyl pyrophosphate (GGPP; a 20-carbon molecule), respectively.

b. The Lower Carotenoid Biosynthetic Pathway

The mushrooms are transformed with vectors containing genes that encode one or more enzymes in the biosynthetic pathway that produces provitamin A carotenoids (β-carotene, α-carotene, γ-carotene, and/or β-cryptoxanthin). GGPP synthesis is common to both carotenogenic and non-carotenogenic organisms. Typically, the formation of phytoene from GGPP represents the first step unique to biosynthesis of $C_{40}$ carotenoids. It is believed that most, or all, mushrooms produce GGPP. Therefore, in a preferred embodiment, mushrooms are transformed with one or more genes that encode enzymes that convert GGPP to one or more provitamin A carotenoids (β-carotene, α-carotene, γ-carotene, and/or β-cryptoxanthin). Although it is believed that most, or all, mushrooms produce GGPP, some mushrooms may produce FPP as a final metabolite of the upper isoprenoid pathway. Therefore, in other embodiments, mushrooms are transformed with vectors containing one or more genes that encode enzymes that convert FPP to one or more provitamin A carotenoids (β-carotene, α-carotene, γ-carotene, and/or β-cryptoxanthin). In these embodiments, the mushrooms are transformed with a vector that contains a gene encoding a GGPP synthetase in addition to the enzymes required for production of provitamin A carotenoids from GGPP. An exemplary gene that encodes for a GGPP synthetase is the bacterial gene, crtE (Misawa, et al., *Jour. Biotechnol.*, 59:169-81 (1998)).

Mushrooms can be transformed with genes that encode enzymes involved in provitamin A production from any suitable source, including, but not limited to, carotenogenic non-photosynthetic prokaryotes (bacteria), carotenogenic photosynthetic prokaryotes or eukaryotes (i.e., cyanobacteria, algae and plants), or carotenogenic non-photosynthetic eukaryotes (i.e., archeae and fungi). Exemplary carotenogenic bacteria include, but are not limited to, *Erwinia* spp. such as *Erwinia uredovora* and *Erwinia herbicola*, *Flavobacterium* spp., *Agrobacterium aurantiacum*, *Myxococcus xanthus*, *Rhodobacter* spp. such as *Rhodobacter capsulatus* and *Rhodobacter sphaeroides*, *Streptomyces griseus*, *Synechococcus* spp., *Synechocystis* spp., *Thermus thermophilus*, *Brevibacterium linens*, *Halobacterium salinarium*, *Alcaligenes* spp., and *Anabaena* spp. Exemplary carotenogenic algae include, but are not limited to, *Dunaliella salina* and *Haematococcus pluvialis*.

In preferred embodiments, carotenogenic fungi are the source of genes to transform mushrooms to produce provitamin A. Transformation of mushrooms with genes of species from the same kingdom is expected to yield optimum expression of the transgenes due to codon optimization. Exemplary carotenogenic fungi include, but are not limited to, *Xanthophyllomyces dendrorhous*, *Mucor circinelloides*, *Phycomyces blakesleeanus* and *Neurospora crassa*.

Synthesis of provitamin A carotenoids from GGPP occurs in three major steps: 1) synthesis of phytoene, 2) dehydrogenation of phytoene, and 3) cyclization of phytoene (FIG. 1). The steps of phytoene dehydrogenation and phytoene cyclization can occur through one or more intermediates, such as ζ-carotene, neurosporene and γ-carotene, as shown in FIG. 1. In preferred embodiments, mushrooms are transformed with genes that encode enzymes that have phytoene synthase, phytoene dehydrogenase and lycopene cyclase activity. These enzymatic steps can be carried out by three separate enzymes, or can be carried out by more or less than three enzymes depending on the source of genes encoding the enzymes. For example, each step (phytoene synthesis, phytoene dehydrogenation and phytoene cyclization) is carried out by a separate enzyme in some organisms, while other organisms contain two enzymes that carry out these three enzymatic steps, as a result of a single enzyme with two enzymatic activities. Exemplary genes suitable for transformation into mushrooms to produce provitamin A are summarized in Table 1, and discussed below.

i. Synthesis of Phytoene

Typically, the formation of phytoene from GGPP represents the first step unique to biosynthesis of $C_{40}$ carotenoids. Phytoene itself is a colorless carotenoid and occurs via condensation of two molecules of GGPP. This reaction is catalyzed by phytoene synthase, which are conserved among the carotenoid-producing organisms, from bacteria to plants. These enzymes are encoded by the crtB genes in bacteria and by the psy genes in plants, algae and cyanobacteria. They are membrane-associated proteins, with a molecular mass of 35-39 kDa, monomeric, dependent on divalent cations and have several conserved regions (Chamovitz, et al., *FEBS Lett.*, 296:305-310 (1992); Dogbo, et al., *Proc. Natl. Acad. Sci.* 85:7054-8 (1988); Misawa, et al., *J. Bacteriol.*, 172: 6704-12 (1990)). The phytoene synthases of plants and algae show small differences in the amino-terminus region due to the presence of a signal peptide responsible for the localization of these enzymes in chloroplasts and chromoplasts (Cunningham, et al., *Annu. Rev. Plant Physiol. Plant Mol. Biol.*, 49:557-83 (1998)).

ii. Dehydrogenation of Phytoene

The dehydrogenation of phytoene is the next step in the biosynthetic pathway of carotenoids. This involves the introduction of a new double bond into the molecule, using the enzyme phytoene dehydrogenase, also associated with the membrane. Usually, the dehydrogenation process is repeated 2-4 times and at each step the number of double bonds duplicates. Regarding this second step, organisms that synthesize carotenoids may be divided in two groups: those with oxygenic photosynthesis (cyanobacteria, algae, plants) and those that lack oxygenic photosynthesis (all other eubacteria, archaea, fungi).

In organisms with oxygenic photosynthesis, the crtP or the pds genes code for phytoene dehydrogenase. This enzyme only carries out two dehydrogenations and ζ-carotene is the final product.

In the case of organisms lacking this type of photosynthesis, the crtI genes encode phytoene dehydrogenase. This enzyme is able to carry out four consecutive dehydrogenations, producing lycopene as a final product. Exceptions are the phytoene dehydrogenase encoded by the crtI genes of *Rhodobacter capsulatus* and *R. sphaeroides*, where this enzyme only carries out three dehydrogenations and generates neurosporene as the main product (Armstrong, *Annu. Rev. Microbiol.*, 51:629-59 (1997)), and *Neurospora crassa*, where the enzyme carries out five dehydrogenations to generate 3,4-dihydrolycopene as an intermediate step in the formation of torulene (Hausmann and Sandman, *Fungal Genet. Biol.*, 30:147-53 (2000)). The enzyme encoded by the crtI genes has less specificity for the substrate than the enzyme codified by the crtP genes.

Phytoene dehydrogenases are enzymes with a molecular mass of 53-69 kDa. The larger ones correspond to fungi (CrtI), with a size that varies over 62-69 kDa. The two types of enzyme (Crtp, CrtI) do not show any homology (Sandmann, *J. Plant Physiol.*, 143:444-447 (1994); Sandmann, *Eur. J. Biochem.*, 223:7-24 (1994)) and their differences are not restricted to the number of dehydrogenations that each may undergo. Also, they differ in terms of their preference for cofactors and in their sensitivity to inhibitors.

The product of the crtP gene has higher specificity for the substrate and can only carry out two dehydrogenations from phytoene. Therefore, additional enzymes must be used to obtain lycopene in the case of organisms with oxygenic photosynthesis. These additional enzymes include the ζ-carotene dehydrogenases encoded by the crtQ or the zds genes. The ζ-carotene dehydrogenases have a very similar size to those of the dehydrogenases encoded by the crtP-type genes and are phylogenetically related to them (Cunningham, et al., *Annu. Rev. Plant Physiol. Plant Mol. Biol.*, 49:557-83 (1998)). Only one exception has been described: the ζ-carotene dehydrogenase of *Anabaena* PCC7120, which is related to the dehydrogenases of the CrtI-type but not with those of the CrtP-type (Linden, et al., *FEMS Microbiol. Lett.*, 106:99-104 (1993)).

The closest similarity between the two types of phytoene dehydrogenases described is found at the amino terminus, where a dinucleotide-binding sequence is located (Pecker, et al., *Proc. Natl. Acad. Sci. U.S.A.*, 89:4962-6 (1992)). Another sequence has also been found close to the carboxy-terminus (PROSITE PS00982), which is typical of the CrtI-type phytoene dehydrogenases. This sequence is also found in other enzymes involved in carotenogenesis, such as the methoxyneurosporene dehydrogenases (crtD gene). Besides the proteins encoded by the crtD and zds genes of *Anabaena*, there is a third type of protein, different to the others in function, that is related to the CrtI-type phytoene dehydrogenases. This protein is the product of the crtO gene, a β-carotene ketolase of *Synechocystis* PCC6803 (Fernandez-Gonzalez, et al., *J. Biol. Chem.*, 272:9728-33 (1997)). Also, a group of 22 amino acids of the CrtP-type enzymes has been suggested as the carotenoid-binding region (Pecker, et al., *Proc. Natl. Acad. Sci. U.S.A.*, 89:4962-6 (1992)). These amino acids are located close to the area corresponding to that occupied by the sequence mentioned for the CrtI proteins.

iii. Cyclization of Lycopene

Although not universal, the cyclization of lycopene is a common step in the synthesis of carotenoids. Following the dehydrogenation of phytoene from ζ-carotene, neurosporene or lycopene, the biosynthesis of carotenoids can take different pathways, depending on the organism involved. Neurosporene can be hydroxylated to produce spheroidene and spheroidenone in the genus *Rhodobacter* (the conversion being carried out by the crtC gene), while in the majority of organisms the substrate for the next enzymatic step is lycopene. The cyclization of lycopene consists of the introduction, in a sequential manner, of a ring (β- or ε-type) at both ends of the molecule, thus varying the total number of double bonds but not the number of conjugated double bonds. The most common ring is the β-type since the ε-type is only found in plants and certain algae (Cunningham, et al., *Annu. Rev. Plant Physiol. Plant Mol. Biol.*, 49:557-83 (1998)). The enzymes that carry out this reaction are called lycopene β-cyclases and lycopene ε-cyclases, respectively.

There are several types of lycopene β-cyclases that are unrelated phylogenetically. In organisms with oxygenic photosynthesis, the lycopene β-cyclases are encoded by the crtL genes and, in organisms without oxygenic photosynthesis, by the crtY or lye genes. Both types of enzyme sequentially introduce two rings for the formation of β-carotene (through γ-carotene) or one ring if they use ζ-carotene as substrate. The CrtY-type proteins have a size of around 43 kDa, while those of the CrtL-type are about 46-56 kDa. The largest ones are those of plants, since they bear a signal peptide for translocation into chloroplasts and chromoplasts.

Both CrtY-type and CrtL-type lycopene cyclases are different in their primary structure. However, three apparently conserved small sequences have been detected: (1) the sequence for binding to cofactors ($DX_4GXGXAX_4A$) (SEQ ID NO:1), (2) the consensus sequence I ($FXYX_4SX_6EXT$) (SEQ ID NO:2) and (3) the consensus sequence II ($GX_2AX_3HPX_2GY$) (SEQ ID NO:3); and there is also a particular hydropathic profile showing areas of probable transmembrane nature (Cunningham, et al., *Plant Cell*, 6:1107-21 (1994); Hugueney, et al., *Plant J.*, 8:417-24 (1995); Pecker, et al., *Plant Mol. Biol.*, 30:807-19 (1996)).

The known crtY and crtL genes encode lycopene cyclases in eubacteria, algae and plants, but none responsible for encoding a lycopene cyclase in fungi has been described.

Verdoes, et al. (Verdoes, et al., *Mol. Gen. Genet.*, 262:453-61 (1999)) described a new enzyme for the biosynthesis of carotenoids encoded by the crtYB gene, in the Basidiomycete *Xanthophyllomyces dendrorhous*, which is a bifunctional protein with phytoene synthase and lycopene cyclase activity. Subsequently, this bifunctional protein was described in the zygomycete *Mucor circinelloides* (encoded by the carp gene) (Velayos, et al., *Eur. J. Biochem.*, 267:5509-19 (2000)), in the Ascomycete *Neurospora crassa* (encoded by the al-2 gene) (Arrach, et al., *Mol. Genet. Genomics*, 266:914-21 (2002)) and in *Phycomyces blakesleeanus* (encoded by the carRA gene) (Arrach, et al., *Proc. Natl. Acad. Sci. U.S.A.*, 98:1687-92 (2001)).

The products of the crtYB, al-2, carRP and carRA genes share two well defined domains. One is responsible for the phytoene synthase activity and is located in the carboxy-terminus region; and the other is responsible for lycopene cyclase activity and is located in the amino-terminus region. Sequence comparison suggests that the domain responsible for phytoene synthase activity is similar to that of the phytoene and squalene synthases of the other carotenogenic organisms. In contrast, the domain responsible for the activity of lycopene cyclase has no homology with the proteins CrtY and CrtL but does have homology with the two proteins responsible for this activity in *Brevibacterium linens*. The activity of lycopene cyclase in this bacterium is the result of the combined action of the crtYc and crtYd gene products.

Peck et al. (Peck, et al., *J. Bacteriol.*, 184:2889-97 (2002)) identified a gene (crtY) that converts lycopene into b-carotene in the archaeal *Halobacterium salinarium*. This gene encodes a membrane protein similar to the lycopene cyclases of *B. linens* and *Mycobacterium aurum* (Krubasik and Sandmann, *Mol. Gen. Genet.*, 263:423-32 (2000); Peck, et al., *J. Bacteriol.*, 184:2889-97 (2002); Velayos, et al., *Eur. J. Biochem.*, 267:5509-19 (2000)) and those of fungi. This protein has two domains that are similar to the proteins of *B. linens* involved in the cyclization of the lycopene, linked by an additional transmembrane segment that allows the topology of each domain to be maintained.

TABLE 1

Exemplary carotenoid biosynthetic genes and enzymes

| Gene | Enzymatic function | Organism and Corresponding NCBI Gene ID or mRNA Accession Number |
|---|---|---|
| Phytoene Synthesis | | |
| crtB | Phytoene synthase | *Agrobacterium aurantiacum* (GeneID: 2649245), *Erwinia herbicola*, *E. uredovora*, *Flavobacterium* sp., *Myxococcus xanthus* Gene ID: 4105207, *Rhodobacter capsulatus*, *R. sphaeroides* (GeneID: 3719279), *Streptomyces griseus* (GeneID: 6209269), *Synechococcus* sp. (GeneID: 6055775, 4260965, 3901910, 5158601, 5147399, 3898023, 1730420), *Synechocystis* sp. (GeneID: 6055775), *Thermus thermophilus* (TTHB104) (GeneID: 3169276, 2776542) |

TABLE 1-continued

Exemplary carotenoid biosynthetic genes and enzymes

| Gene | Enzymatic function | Organism and Corresponding NCBI Gene ID or mRNA Accession Number |
|---|---|---|
| crtYB | Phytoene synthase | (Armstrong, *Annu. Rev. Microbiol*, 51: 629-59 (1997) *Xanthophyllomyces dendrorhous* (Accession Nos. AY177204.1, AY174117.1)(Verdoes, et al., *Mol. Gen. Genet.*, 262: 453-61 (1999) |
| carRP | Phytoene synthase | *Mucor circinelloides* (Accession No. AJ250827) (Velayos, et al., *Eur. J. Biochem.*, 267: 5509-19 (2000)) |
| carRA | Phytoene synthase | *Phycomyces blakesleeanus* (Accession Nos. AJ278287, AJ276965) (Arrach, et al., *Proc. Natl Acad. Sci. U.S.A.*, 98: 1687-92 (2001)); *Blakeslea trispora* (Accession Nos. AY176663, AY176662) (Rodriguez-Saiz, et al., *Appl Env. Microbiol.*, 70: 5589-94 (2004)) |
| al-2 | Phytoene synthase | *Neurospora crassa* (Gene ID: 2706945) (Attach, et al., Mol. Genet. Genomics, 266: 914-21 (2002)) |
| psy | Phytoene synthase | *Haematococcus pluvialis* (Accession No. AY835634) (Steinbrenner and Linden, *Plant Physiol.*, 125: 810-7 (2001)) |
| Dehydrogenation of phytoene | | |
| crtI | Phytoene dehydrogenase | *A. aurantiacum, E. herbicola, E. uredovora, Flavobacterium* sp., *M. xanthus* (GeneID: 4103765), *R. capsulatus, R. sphaeroides* (GeneID: 3719280, 7358935), *S. griseus* (GeneID: 6216102) (Armstrong, *Annu. Rev. Microbiol.*, 51: 629-59 (1997) |
| crtP | Phytoene dehydrogenase | *Synechococcus* sp. (GeneID: 6055773), *Synechocystis* sp. (Armstrong, *Annu. Rev. Microbiol*, 51: 629-59 (1997) |
| crtQ | ζ-carotene dehydrogenase | *Anabaena* sp. (Accession No. Y15115) (Armstrong, *Annu. Rev. Microbiol*, 51: 629-59 (1997) |
| carB | Phytoene dehydrogenase | *Blakeslea trispora* (Accession Nos. AY884174, AY176663, AY176662) (Rodriguez-Saiz, et al., *Appl. Env. Microbiol.*, 70: 5589-94 (2004)) |
| pds | Phytoene dehydrogenase | *Haematococcus pluvialis* (Accession No. AY768691) (Steinbrenner and Linden, *Plant Physiol*, 125: 810-7 (2001)) |
| zds | ζ-carotene dehydrogenase | *Haematococcus pluvialis* (Steinbrenner and Linden, *Plant Physiol.*, 125: 810-7 (2001)) |
| Lycopene cyclization | | |
| crtY | Lycopene cyclase | *A. aurantiacum, E. herbicola, E. uredovora, Flavobacterium* sp., *S. griseus* (GeneID: 6210292) (Armstrong, *Annu. Rev. Microbiol.*, 51: 629-59 (1997) |
| crtL | Lycopene cyclase | *Synechococcus* sp. (GeneID: 5148330, 4260776, 3742414, 3736609, 5158352, 1730491, 6056861) Armstrong, (*Annu. Rev. Microbiol.*, 51: 629-59 (1997) |
| crtYc, crtYd | Lycopene cyclase | *Brevibacterium linens* (Accession No. AF139916) (Krubasik, et al., *Mol. Gen. Genet.*, 263: 423-32 (2000)) |
| crtY | Lycopene cyclase | *Halobacterium salinarium* (GeneID: 5953587) (Peck, et al., *J. Bacterial.*, 184: 2889-98 (2002)) |
| crtYB | Lycopene cyclase | *X. dendrorhous* (Verdoes, et al., *Mol. Gen. Genet.*, 262: 453-61 (1999) |
| carRP | Lycopene cyclase | *Mucor circinelloides* (Accession No. AJ250827) (Velayos, et al., *Eur. J. Biochem.*, 267: 5509-19 (2000)) |
| carRA | Lycopene cyclase | *Phycomyces blakesleeanus* (Accession Nos. AJ278287, AJ276965) (Arrach, et al., *Proc. Natl. Acad. Sci. U.S.A.*, 98: 1687-92 (2001)); *Blakeslea trispora* (Accession Nos. AY176663, AY176662) (Rodriguez-Saiz, et al., *Appl. Env. Microbiol,* 70: 5589-94 (2004)) |
| al-2 | Lycopene cyclase | *N. crassa* (Accession No. BX842641) (Arrach, et al., *Mol. Genet. Genomics,* 266: 914-21 (2002)) |
| lcyb | Lycopene cyclase | *Haematococcus pluvialis* (Steinbrenner and Linden, *Plant Physiol.*, 125: 810-7 (2001)) |

Mushrooms can be transformed with genes encoding enzymes that have phytoene synthase, phytoene dehydrogenase and lycopene cyclase activities obtained from the same or from different species. In a preferred embodiment, genes encoding enzymes that have phytoene synthase, phytoene dehydrogenase and lycopene cyclase activities are obtained from the same donor species. Mushrooms can be additionally transformed with one or more additional genes that encode for enzymes that convert β-carotene or a metabolic intermediate into one or more additional provitamin A carotenoids.

In some embodiments, a transgene is constructed to encode a multifunctional enzyme through gene fusion techniques in which the coding sequences of different genes are fused with or without linker sequences to obtain a single gene encoding a single protein with the activities of the individual genes. In this manner, for example, a fusion protein containing both phytoene synthase and phytoene dehydrogenase activities can be generated.

3. Genes from Non-Photosynthetic Prokaryotes

In some embodiments, mushrooms are transformed with genes from non-photosynthetic bacteria that encode enzymes that convert GGPP to one or more provitamin A carotenoids. As set forth above and in Table 1, the bacterial genes encoding phytoene synthase, phytoene dehydrogenase, and lycopene cyclase are CrtB, CrtI and CrtY, respectively. In one embodiment, mushrooms are transformed with the bacterial crtB, crtI and crtY genes to convert GGPP to β-carotene. In other embodiments, mushrooms that produce FPP as a final metabolite of the upper isoprenoid pathway are additionally transformed with the bacterial crtE gene. In other embodiments, mushrooms are transformed with the bacterial crtB, crtI and crtY, and, optionally, crtE genes, and are additionally transformed with one or more additional genes that encode for enzymes that convert α-carotene into one or more additional provitamin A carotenoids.

crtB, crtI and crtY genes can individually be obtained from the same or from different species of non-photosynthetic bacteria. In a preferred embodiment, crtB, crtI and crtY genes are obtained from the same species of non-photosynthetic bacteria.

4. Genes from Non-Photosynthetic Eukaryotes

In some embodiments, mushrooms are transformed with genes from non-photosynthetic eukaryotes that encode enzymes that convert GGPP to one or more provitamin A carotenoids. As set forth above and in Table 1, phytoene synthase and lycopene cyclase activities are generally carried out by a single gene product in non-photosynthetic eukaryotes, while a separate gene product has phytoene dehydrogenase activity. Suitable genes that encode for enzymes with these activities are provided in Table 1.

Genes that encode enzymes that convert GGPP to one or more provitamin A carotenoids for transformation of mushrooms can individually be obtained from the same or from different species of non-photosynthetic eukaryote. In a preferred embodiment, the genes are obtained from the same species of non-photosynthetic eukaryote.

5. Genes from Photosynthetic Prokaryotes and Eukaryotes

In some embodiments, mushrooms are transformed with genes from photosynthetic prokaryotes or eukaryotes that encode enzymes that convert GGPP to one or more provitamin A carotenoids. As set forth above and in Table 1, the genes encoding phytoene synthase are crtB and psy for photosynthetic prokaryotes and photosynthetic eukaryotes, respectively. Phytoene dehydrogenase activity is encoded by the crtP and crtQ genes in photosynthetic prokaryotes and by the pds and zds genes in photosynthetic eukaryotes. Lycopene cyclase is encoded by the crtL and lcyb genes in photosynthetic prokaryotes and photosynthetic eukaryotes, respectively.

In some embodiments, mushrooms are transformed with the crtB, crtP, crtQ and crtL genes from photosynthetic prokaryotes to convert GGPP to β-carotene. In other embodiments, mushrooms that produce FPP as a final metabolite of the upper isoprenoid pathway are additionally transformed with the bacterial crtE gene.

In still other embodiments, mushrooms are transformed with the psy, pds, zds and lcyb genes from photosynthetic eukaryotes to convert GGPP to β-carotene. In other embodiments, mushrooms that produce FPP as a final metabolite of the upper isoprenoid pathway are additionally transformed with the bacterial crtE gene.

6. Combinatorial Gene Sources

In some embodiments, mushrooms are transformed with genes derived from more than one donor organism that are of the same or different genus or species. The genes can be derived from any combination of prokaryotic or eukaryotic species. The genes can also be derived from any combination of photosynthetic or non-photosynthetic species.

C. Homologs, Variants, Fragments and Codon Optimization

Homologs, variants and/or fragments of any of the genes described above can be used provided that the homologs, variants and/or fragments encode for polypeptides that retain phytoene synthase, phytoene dehydrogenase or lycopene cyclase enzymatic activity. Preferred variants are conservatively modified variants.

The coding sequence of the genes to be transformed into mushrooms can also be modified to enhance its expression in mushrooms in a process referred to as "codon optimization". The genetic code is redundant with 64 possible codons, but most organisms preferentially use a subset of these codons. The codons that are utilized most often in a species are called optimal codons, and those not utilized very often are classified as rare or low-usage codons (Zhang, et al., *Gene,* 105: 61-72 (1991)). In particular, gene expression in basidiomycetes requires a certain nucleotide composition (Schuren and Wessels, *Curr. Genet.,* 33:151-6 (1998); Lugones, et al., *Mol. Microbiol.,* 32:681-9 (1999); Ma, et al., *Appl. Environ. Microbiol.,* 67:948-55 (2001); Scholtmeijer, et al., *Appl. Environ. Microbiol.,* 67:481-3 (2001)). Preferably, the genes encoding provitamin A biosynthetic activity to be transformed into mushrooms have a G/C content of at least 50% and no, or minimal, stretches of about 10 nucleotides or less with more than 90% A or T.

D. Genes that Confer Additional Traits

Mushrooms can also be transformed with genes that confer additional desirable traits, such as increased resistance to pests and diseases, increased resistance to drought, or modified fatty acid production.

1. Increased Fatty Acid Synthesis

The bioavailability of the carotenoids varies depending on absorption and on their yield of retinol. Only 40-60% of ingested beta carotene from plant sources is absorbed by the human body, whereas 80-90% of retinyl esters from animal proteins are absorbed. Carotenoid absorption is affected by dietary factors, including zinc deficiency, a low-fat diet, lipid malabsorption, abetalipoproteinemia, and protein deficiency. Provitamin A carotenoids are fat soluble, and their absorption can be increased by co-ingestion with fatty acids. In some embodiments, mushrooms transformed with genes encoding provitamin A biosynthetic enzymes are also transformed with genes encoding proteins that increase the production of fatty acids relative to non-transgenic mushrooms of the same species.

2. Increased Resistance to Pests

Fly pests are a constant threat to the successful commercial production of mushrooms. Uncontrolled populations of any of these pests cause losses in yield both directly by the activity of the larvae and indirectly by adult flies spreading fungal and bacterial diseases. Common mushroom pests include, sciarids, such as *Lycoriella castanescens* (*auripila*), *L. ingenues* (*mali*), *Bradysia. difformis* (*paupera*) and *B. lutaria*, phorids, such as *Megaselia halterata*, cecids, such as *Heteropeza pygmaea* and *Mycophila speyeri*, and sphaerocerids, such as *Pullimosina heteroneura*.

In some embodiments, mushrooms selected for increased resistance to pests are used for transformation with genes encoding provitamin A biosynthetic enzymes. Mushrooms selected for increased resistance to pests can be species of mushroom that are more resistant to pests than other species of mushroom, or can be particular isolates of a single species of mushroom that are more resistant to pests than other isolates of the same species of mushroom. The pest resistant mushrooms can be naturally occurring, or can be isolated by growing mushrooms in the presence of pests, and then selecting for those that have the best growth.

In other embodiments, mushrooms transformed with genes encoding provitamin A biosynthetic enzymes are also transformed with genes encoding proteins that confer resistance to mushroom pests, such as flies.

3. Increased Resistance to Drought

Mushrooms are very sensitive to changes in natural conditions, such as temperature, moisture and habitat, and will lie dormant until conditions permit adequate propagation. Mushrooms are particularly sensitive to moisture conditions. Therefore, in some embodiments, mushrooms selected for drought resistance are used for transformation with genes encoding provitamin A biosynthetic enzymes. Mushrooms selected for drought resistance can be species of mushroom that are more resistant to drought than other species of mushroom, or can be particular isolates of a single species of mushroom that are more resistant to drought than other isolates of the same species of mushroom. The drought resistant mushrooms can be naturally occurring, or can be isolated by growing mushrooms under drought conditions, and then selecting for those that have the best growth.

In other embodiments, mushrooms transformed with genes encoding provitamin A biosynthetic enzymes are also transformed with genes encoding proteins that confer increased resistance to drought relative to non-transgenic mushrooms.

III. Transformation of Mushrooms with Genes for Provitamin A Carotenoid Production Transgenic mushrooms for producing provitamin A carotenoids can be produced using conventional techniques to express heterologous genes in mushrooms or mushroom cells. Typically, gene transfer is carried out using explants capable of regeneration to produce complete, fertile mushrooms. Generally, a DNA molecule, such as a gene, to be introduced into the mushroom is part of a vector, such as a transformation vector. A large number of such vector systems known in the art may be used, such as plasmids.

Transformation vectors contain an expression cassette that includes the coding sequence of the gene to be expressed operably linked to a promoter suitable to drive expression of the gene in mushrooms. The expression cassette preferably also contains a transcriptional terminator, and at least one selectable marker to allow for selection of transformants. Expression cassettes can also contain additional sequences, including introns and sequences intended for targeting of the gene product to specific organelles or cell compartments.

Genes encoding provitamin A carotenoid biosynthetic enzymes for are preferably stably transformed and integrated into the genome of the host cells. Transformed cells are preferably regenerated into whole mushrooms. Detailed description of transformation techniques are within the knowledge of those skilled in the art.

A. Expression Cassettes

1. Genes

The expression cassettes contain one or more genes that encode for enzymes involved in provitamin A biosynthesis. The genes may be any described above. Genes encoding for enzymes involved in provitamin A biosynthesis can include non-translated sequences (e.g., introns) within translated regions of the nucleic acid, or may lack such intervening non-translated sequences (e.g., as in cDNA). A single expression cassette can contain one or more genes encoding enzymes involved in provitamin A biosynthesis. The genes can be the same or different and can be arranged in the expression cassette such that they are operably linked to one or more promoters. For example, two or more copies of the same gene (i.e., crtB) can be arranged in tandem behind a single promoter, or two or more copies of the same gene can be present, each operably linked to a separate promoter. Alternatively, the expression cassette can contain copies of different genes (i.e., crtB and crtI) which are each operably linked to a single promoter, or separate promoters.

2. Promoters

Expression cassettes contained in vectors used to transform mushrooms containing genes encoding enzymes for provitamin A carotenoid biosynthesis include promoters operably linked to the genes to drive their expression. Any promoter that causes expression in mushrooms can be used to drive expression of genes encoding enzymes for provitamin A carotenoid biosynthesis. Useful promoters can be derived from eukaryotes, prokaryotes or viruses. Promoters useful for expression in fungi are known in the art and can be constitutive, inducible, or tissue-specific. Many suitable promoters for fungi are known in the art, and their sequences are available through sources such as Genbank.

Promoters (and other regulatory elements) may be heterologous (i.e., not naturally operably linked to a DNA sequence from the same organism). In preferred embodiments, the promoter is homologous to the recipient host cell species. It may also be desirable to include some intron sequences in the promoter constructs since the inclusion of intron sequences in the coding region may result in enhanced expression and specificity. Downstream sequences that further serve to enhance binding to the promoter or otherwise enhance expression of transgenic sequences can also be added. Additionally, regions of one promoter may be joined to regions from a different promoter in order to obtain the desired promoter activity resulting in a chimeric promoter. Synthetic promoters that regulate gene expression may also be used.

a. Constitutive Promoters

In some embodiments, genes encoding enzymes for provitamin A carotenoid biosynthesis are operably linked to constitutive promoters. Exemplary fungi specific promoters include, but are not limited to, the glyceraldehyde 3-phosphate dehydrogenase (gpdA) promoters from the fungi *A. nidulans*, (Mattern, et. al., *Fungal Genetics Newsletter*, 35:25 (1988)), and *A. bisporus* (Harmsen, et. al., *Current Genetics*, 22:447-454 (1992)). Other suitable constitutive promoters for expression in fungi include, but are not limited to, phosphoglycerate kinase (pgk) promoter, the pyruvate kinase (pki) promoter, TPI, the triose phosphate isomerase (tpi) promoter, the APC synthetase subunit g (oliC) promoter and the acetamidase (amdS) promoter of a basidiomycete (see, for example, WO96/41882). The promoters can include the full promoter, or any part thereof that is sufficient to drive expression of the gene operably linked thereto.

b. Inducible Promoters

In other embodiments, genes encoding enzymes for provitamin A carotenoid biosynthesis are operably linked to inducible promoters (Ward et al. *Plant Mol. Biol.*, 22:361-366 (1993)). Inducible promoters can be used to modulate the expression of a gene in a mushroom through the application of an exogenous chemical regulator. Depending upon the objective, the promoter can be a chemically-inducible promoter, where application of the chemical induces gene expression, or a chemically-repressible promoter, where application of the chemical represses gene expression. Inducible promoters allow for expression of operably linked genes during controlled periods. For example, gene expression can be induced in a mature mushroom following development of a fruiting body.

Exemplary inducible promoters include, but are not limited to, that from the ACEI system which responds to copper (Mett, et al., *Proc. Natl. Acad. Sci. U.S.A.*, 90:4567-4571 (1993)); In2 gene from maize which responds to benzenesulfonamide herbicide safeners (Hershey, et al., *Mol. Gen. Genetics*, 227:229-237 (1991); Gatz, et al., *Mol. Gen. Genetics*, 243:32-38 (1994)) or Tet repressor from Tn10 (Gatz, et al., *Mol. Gen. Genet.*, 227:229-237 (1991). Preferred inducible promoters are promoters that respond to an inducing agent to which fungi do not normally respond. An exemplary inducible promoter is the inducible promoter from a steroid hormone gene, the transcriptional activity of which is induced by a glucocorticosteroid hormone (Schena, et al., *Proc. Natl. Acad. Sci. U.S.A.*, 88:0421 (1991)).

Other exemplary inducible promoters include the basidiomycete promoters of the following genes: xylanase A (xylA), glucoamylase A (glaA), cellobiohydrolase (cbh), amylase (amy), invertase (suc), TAKA amylase and amyloglucosidase (ACT) (see, for example, WO96/41882).

c. Tissue-Specific Promoters

In other embodiments, genes encoding enzymes for provitamin A carotenoid biosynthesis are operably linked to tissue-specific or developmentally regulated promoters. A tissue-specific or developmentally regulated promoter is a DNA sequence that regulates the expression of an operably linked gene selectively in the cells/tissues critical to a particular developmental period and/or function in the mushroom.

Developmentally regulated fungal promoters that can be used for expression of heterologous genes in a basidiomycete include, but are not limited to, the abstl, rafe and mag2 genes of *Agaricus bisporus*, which are active substantially only during stage 1, or later, of the development of the fruiting body of the fungus (WO2004/039985). Heterologous genes under the control of these promoters allows for selective expression at this stage of development of the fungus, rather than during growth of the mycelium. In that way, little or no metabolic energy need be diverted from mycelium growth, thereby maximizing fruiting body mass and concomitant tissue capable of expressing the heterologous gene once it is switched on.

3. Reporter Genes and Selectable Marker Genes

Expression cassettes preferably additionally contain selection marker genes that encode a selection gene product conferring on a cell resistance to a chemical agent or physiological stress, or confers a distinguishable phenotypic characteristic to the cells such that cells transformed with the expression cassette may be easily selected using a selective agent. Multiple reporter genes or selectable markers can be used to select for mushrooms or mushroom cells transformed with multiple genes of interest.

One such selection marker gene is neomycin phosphotransferase (NPT II), which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed mushroom. Polymerase chain reaction (PCR) amplification is also used to identify the presence of a transgene or expression using reverse transcription-PCR amplification to monitor expression and PCR on genomic DNA. Other commonly used selection markers include the ampicillin resistance gene, the tetracycline resistance and the hygromycin (HPH) resistance gene.

Other suitable selectable marker genes include, but are not limited to, genes encoding resistance to chloramphenicol (Herrera Estrella, et al., *EMBO J.* 2:987-992 (1983); methotrexate (Herrera Estrella, et al., *Nature*, 303:209-213 (1983); Meijer, et al., *Plant Mol. Biol.*, 16:807-820 (1991)); hygromycin (Waldron, et al., *Plant Mol. Biol.*, 5:103-108 (1985); Zhijian, et al., *Plant Science*, 108:219-227 (1995)); streptomycin (Jones, et al., *Mol. Gen. Genet* 210:86-91 (1987)); spectinomycin (Bretagne-Sagnard, et al., *Transgenic Res.*, 5:131-137 (1996)); bleomycin (Hille, et al., *Plant Mol. Biol.*, 7:171-176 (1990)); sulfonamide (Guerineau, et al., *Plant Mol. Biol.*, 15:127-136 (1990)); bromoxynil (Stalker, et al., *Science*, 242:41 9423 (1988)); glyphosate (Shaw, et al., *Science*, 233:478481 (1986)); phosphinothricin (DeBlock, et al., *EMBO J.*, 6:2513-2518 (1987)).

4. Other Regulatory Elements

The expression system may be further optimized by employing supplemental elements such as transcription terminators, enhancer elements, and/or internal ribosome entry site (IRES) elements.

In addition to a promoter sequence, an expression cassette or polynucleotide construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium octopine* synthase signal (Gielen, et al., *EMBO J.*, 3:835-846 (1984)) or the nopaline synthase signal (Depicker, et al., *Mol. and Appl. Genet.*, 1:561-573 (1982)).

Transport of protein produced by transgenes to a subcellular compartment such as the vacuole, peroxisome, glyoxysome, cell wall or mitochondrion, or for secretion into the apoplast or growth medium, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately located. The presence of a signal sequence directs a polypeptide to either an intracellular organelle or subcellular compartment or for secretion to the apoplast or into the external, environment. Many signal sequences are known in the art.

In certain embodiments, internal ribosome entry site (IRES) elements are used to create multigene, or polycistronic, messages. IRES elements are able to bypass the ribosome scanning model of 5' methylated cap dependent translation and begin translation at internal sites (Pelletier and Sonenberg, *Nature*, 334(6180):320-325 (1988)). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

C. Transformation Protocols

Any suitable method for transformation of mushrooms can be used to generate mushrooms containing genes that encode enzymes in provitamin A carotenoid biosynthetic pathways. Suitable transformation methods include, but are not limited to, transformation of naked DNA with or without a carrier, such as polyethylene glycol or $CaCl_2$, electroporation, particle bombardment, and *Agrobacterium*-mediated transformation (WO 95/02691; WO 98/45455; Li and Horgen, *Cult. Mush. Newsl.*, 1:11-6 (1993); van der Rhee, et al., *Mol. Gen. Genet.*, 250:252-8 (1996); van der Rhee, et al., *Curr. Genet.*, 30:166-73 (1996); Alves, et al., *App. Env. Microbiol.*, 70:6379-84 (2004); Gouka, et al., *Nat. Biotechnol.*, 17:598-601 (1999); Guerche, et al., *Plant Sci.*, 52:111-6 (1987); Godio, et al., *Curr. Genet.*, 46:287-94 (2004); Schuurs, et al.,

*Genetics*, 147:589 (1997)). Preferred methods of transformation to generate transgenic mushrooms containing enzymes for vitamin A biosynthesis are dependent on the species of mushroom to be transformed. For species of mushroom that can be transformed by simple naked DNA transfection, such as oyster mushrooms (*Pleurotus ostreatus*), this is a preferred method, because it is expedient and inexpensive. In other embodiments, *Agrobacterium*-mediated transformation is a preferred method to transform mushroom species, such as button mushrooms (*Agaricus bisporus*), that are relatively resistant to transformation by naked DNA transfection alone.

Methods for transforming mushrooms using *Agrobacterium*-mediated transformation are known in the art (Chen, et al., *App. Env. Microbiol.*, 66:4510-3 (2000); De Groot, et al., *Nat. Biotechnol.*, 16:839-42 (1998); Mikosch, et al., *Curr. Genet.*, 39:35-39 (2001)). Generally, strains of bacteria, such as *Agrobacterium tumefaciens*, are used for genetic transformation that transfer part of its Ti plasmid to plants during tumorigenesis. Typically, the *Agrobacterium* used harbors modified versions of the naturally occurring Ti plasmid in which the oncogenes and the opaline metabolism genes have been removed such that the DNA is transferred to the host cells without the subsequent formation of tumors. These methods involve the insertion within the borders of the Ti plasmid the DNA to be inserted into the cellular genome linked to a selection marker gene to facilitate selection of transformed cells. Bacteria and recipient tissues are cultured together to allow transfer of foreign DNA into mushroom cells then transformed cells are regenerated on selection media.

The use of supervirulent *A. tumefaciens* strains is preferred, because they give a relatively high transformation frequency, such strains, the use thereof and vectors for making such strains are described in the literature (Jin, et al., *J. Bacteriology*, 169:4417-4425 (1987); Raineri, et al., *Biotechnology*, 8:33-38 (1990); Ishida, et al., *Nature Biotechnology*, 14:745-750 (1996); Piers, et al., *Proc. Natl. Acad. Sci. USA*, 93 1613-1618 (1996)).

Any suitable mushroom cells or tissues can be used as host cells for transformation, including, but not limited to, protoplasts, spores, vegetative mycelium and fruit body tissue. In a preferred embodiment, fruit body tissue is used. Fruit body tissue used for transformation preferably contains gill tissue.

Following transformation by any one of the methods described above, the following procedures can be used to obtain a transformed mushroom expressing the transgenes: select the mushroom cells that have been transformed on a selective medium; regenerate the mushroom cells that have been transformed to produce mature mushrooms; select transformed mushrooms expressing the transgenes producing the desired level of desired enzymes. The cells that have been transformed may be grown into mushrooms in accordance with conventional techniques. Transformed mushroom cells thus selected can grow and develop into the vegetative mycelium, which will eventually yield the whole fungus, including the sexual reproductive structure (fruit body) and spores.

IV. Methods of Use

The transgenic mushroom disclosed herein can be used as a source of provitamin A. Provitamin A can be obtained from the mushrooms by ingesting the mushroom, or alternatively, provitamin A can be isolated from the mushrooms for use as a supplement. Biochemical methods for preparation of provitamin A from plants and other sources are well known in the art. In a preferred embodiment, provitamin A is obtained from the transgenic mushrooms by ingestion of all or part of the mushroom, such as the fruiting body.

In some embodiments, provitamin A produced by the disclosed transgenic mushrooms is used as a therapeutic. Transgenic mushrooms producing provitamin A carotenoids, or provitamin A carotenoids isolated therefrom can be administered, preferably orally, to a subject in an effective amount to treat, alleviate, reduce or inhibit one or more symptoms of a disease or disorder associated with vitamin A deficiency (VAD). The USDA daily recommended allowance of vitamin A is 400-500 retinol activity equivalents (RAE) for infants, 300-400 RAE for children, 600-900 RAE for adult males, 600-700 RAE for adult females, 750-770 RAE for pregnant females, and 1,200-1,300 RAE for lactating females. In some embodiments, the transgenic mushrooms provide at least 400; 500; 600; 700; 800; 900; 1,000; 1,100; 1,200; or more RAE. In one embodiment, an individual ingests an effective amount of the transgenic mushrooms described herein to reach the USDA daily recommended allowance for the particular individual.

Transgenic rice engineered to produce provitamin A have been reported to contain between about 1 and about 20 μg of carotenoid per gram dry weight of endosperm (Paine, et al., *Nature Biotechnology*, 23(4):482-7 (2005)). In some embodiments, the transgenic mushrooms contain at least 1, 2, 3, 4, 5, 10, 15, 20, 25, 30, 35, 40, 45, 50 μg or more of provitamin A carotenoid per gram dry weight of mushroom.

Deficiency of vitamin A is found among malnourished, elderly, and chronically sick populations in the United States, but it is more prevalent in developing countries. The risk of VAD is increased in patients suffering from fat malabsorption, cystic fibrosis, sprue, pancreatic insufficiency, IBD, or cholestasis, as well as in persons who have undergone small-bowel bypass surgery. The risk is also increased in vegans, persons with alcoholism, and toddlers and preschool children living below the poverty line.

The one or more symptoms of a disease or disorder associated with vitamin A deficiency (VAD) that can be reduced or inhibited by ingesting the transgenic mushrooms described herein include, but are not limited to, blindness, abnormal visual adaptation to darkness (nyctalopia), dry skin, dry hair, broken fingernails, impairment of the humoral and cell-mediated immune system, bitot spots, pruritus, keratomalacia, xerophthalmia, corneal perforation, follicular hyperkeratosis (phrynoderma), excessive deposition of periosteal bone, anemia, and keratinization of mucous membranes.

Abnormal visual adaptation to darkness, dry skin, dry hair, broken fingernails, and decreased resistance to infections are among the first signs of VAD (Russell, *Harrison's Principles of Internal Medicine*. Braunwald E, Fauci A, Kasper D, et al, eds. vol 1. 15$^{th}$ ed. New York, N.Y.: McGraw-Hill; 2001:465-6).

Other symptoms of vitamin A deficiency include the following: bitot spots, which are areas of abnormal squamous cell proliferation and keratinization of the conjunctiva, can be seen in young children with VAD; blindness due to retinal injury; poor adaptation to darkness (nyctalopia); pruritus; keratomalacia; xerophthalmia; corneal perforation; follicular hyperkeratosis (phrynoderma) secondary to blockage of hair follicles with plugs of keratin; excessive deposition of periosteal bone secondary to reduced osteoclastic activity; anemia; keratinization of mucous membranes; and impairment of the humoral and cell-mediated immune system.

Vitamin A has a major role in phototransduction. The cone cells are responsible for the absorption of light and for color vision in bright light. The rod cells detect motion and are responsible for night vision. In the rod cells of the retina, all-trans-retinol is converted into 11-cis-retinol, which then combines with a membrane-bound protein called opsin to yield rhodopsin. A similar type of reaction occurs in the cone cells of the retina to produce iodopsin. The visual pigments absorb light at different wavelengths, according to the type of cone cell they occupy. VAD leads to a lack of visual pigments; this reduces the absorption of various wavelengths of light, resulting in blindness.

Night blindness caused by VAD has been associated with the loss of goblet cells in the conjunctiva, a membrane covering the outer surface of the eye. Goblet cells are responsible for secretion of mucus, and their absence results in xerophthalmia, a condition where the eyes fail to produce tears. Dead epithelial and microbial cells accumulate on the conjunctiva and form debris that can lead to infection and possibly blindness.

1. Forms

In some embodiments, the mushrooms are used to produce a feedstock for human or animal consumption. The feedstock can include the whole mushroom, or any edible part thereof, including, but not limited to, spores, fruiting bodies, stems, caps, or vegetative mycelium. Preferably the feedstock provides at least 400; 500; 600; 700; 800; 900; 1,000; 1,100; 1,200; or more RAE when ingested by a subject.

The mushrooms may be ingested as a whole mushroom or any portion thereof, such as the fruiting body.

The mushrooms may be dried prior to ingestion.

In one embodiment, the mushrooms, or provitamin A purified therefrom can be formed into a powder. Optionally, the powdered mushroom or provitamin A is included in an oral dosage form, such as a capsule or tablet, along with other suitable carriers and excipients.

Alternatively, the mushrooms may be cooked and combined with other foodstuffs prior to ingestion.

2. Co-Treatments

The transgenic mushrooms can be used in combination with one or more additional compositions to treat, alleviate, reduce, and/or inhibit one or more symptoms of a disease or disorder associated with VAD. In some embodiments, the additional composition is another source of provitamin A, such as another foodstuff, or a supplement. In other embodiments, the additional composition is a source of fatty acids that increase the absorption of consumed provitamin A.

In other embodiments, the disclosed transgenic mushrooms, or provitamin A obtained therefrom, can be combined with other vitamins and/or other nutrients, including, but not limited to, biotin, choline, folate, niacin, pantothenic acid, riboflavin, thiamin, vitamin B6, vitamin B12, vitamin C, vitamin D, vitamin E, and vitamin K.

I claim:

1. A transgenic mushroom genetically engineered to produce provitamin A carotenoids selected from the group consisting of α-carotene, β-carotene, and γ-carotene.

2. The transgenic mushroom of claim 1, wherein the mushroom is a basidiomycete.

3. The transgenic mushroom of claim 2, wherein the basidiomycete is selected from the group consisting of *Agaricus arvensis, Agaricus bisporus, Agaricus blazei, Agrocybe aegerita, Coprinus cinereus, Lentinus edodes, Lepista nuda, Pleurotus ostreatus, Phanerochaete chrysosporium, Schizophyllum commune, Hypsizygus tessulatus, Pholiota nameko, Boletus edulis, Flammulina velutipes, Hericium erinacelus, Volvariella volvacea, Grifola frondosa, Ganoderma lucidum, Tremella fuciformis, Auricularia auricular, Lyophyllum descastes, Naemataloma sublaterium, Stropharia rugoso-annulata* and *Cordyceps sinense*.

4. The transgenic mushroom of claim 3, wherein the basidiomycete is *Pleurotus ostreatus*.

5. The transgenic mushroom of claim 1, wherein the transgenic mushroom comprises genes encoding enzymes that convert geranylgeranyl pyrophosphate (GGPP) to one or more provitamin A carotenoids.

6. A transgenic mushroom genetically engineered to produce provitamin A carotenoids, wherein the transgenic mushroom comprises genes encoding enzymes that convert geranylgeranyl pyrophosphate (GGPP) to one or more provitamin A carotenoids, and wherein the genes encoding enzymes that convert geranylgeranyl pyrophosphate (GGPP) to one or more provitamin A carotenoids comprise genes that encode for enzymes that have phytoene synthase, phytoene dehydrogenase, and lycopene cyclase activity.

7. The transgenic mushroom of claim 6, wherein the genes encoding for enzymes that have phytoene synthase, phytoene dehydrogenase, and lycopene cyclase activity are derived from an organism that is selected from the group consisting of a non-photosynthetic eukaryote, a non-photosynthetic prokaryote, a photosynthetic prokaryote and a photosynthetoc eukaryote.

8. The transgenic mushroom of claim 7, wherein the genes encoding for enzymes that have phytoene synthase, phytoene dehydrogenase, and lycopene cyclase activity are derived from a non-photosynthetic prokaryote.

9. The transgenic mushroom of claim 8, wherein the genes comprise crtB, crtI and crtY, or homologs, variants or fragments thereof that encode enzymes that retain phytoene synthase, phytoene dehydrogenase, or lycopene cyclase activity.

10. The transgenic mushroom of claim 7, wherein the genes encoding for enzymes that have phytoene synthase, phytoene dehydrogenase, and lycopene cyclase activity are derived from a non-photosynthetic eukaryote.

11. The transgenic mushroom of claim 10, wherein a single gene encoding for an enzyme that has phytoene synthase and lycopene cyclase activities.

12. The transgenic mushroom of claim 7, wherein the genes encoding for enzymes that have phytoene synthase, phytoene dehydrogenase, and lycopene cyclase activity are derived from a photosynthetic prokaryote.

13. The transgenic mushroom of claim 12, wherein the genes comprise crtB, crtP, crtQ and crtL, or homologs, variants or fragments thereof that encode enzymes that retain phytoene synthase, phytoene dehydrogenase, or lycopene cyclase activity.

14. The transgenic mushroom of claim 7, wherein the genes encoding for enzymes that have phytoene synthase, phytoene dehydrogenase, and lycopene cyclase activity are derived from a photosynthetic eukaryote.

15. The transgenic mushroom of claim 14, wherein the genes comprise psy, pds, zds and lcyb, or homologs, variants or fragments thereof that encode enzymes that retain phytoene synthase, phytoene dehydrogenase, or lycopene cyclase activity.

16. The transgenic mushroom of claim 5, wherein the transgenic mushroom further comprises a gene encoding an enzyme that converts farnesyl pyrophosphate (FPP) to geranylgeranyl pyrophosphate (GGPP).

17. A method for producing a transgenic mushroom that produces provitamin A carotenoids comprising transforming a mushroom cell or tissue with genes encoding enzymes that convert geranylgeranyl pyrophosphate (GGPP) to one or more provitamin A carotenoids selected from the group consisting of β-carotene, α-carotene, and γ-carotene.

18. The method of claim 17, wherein the mushroom cell or tissue is transformed by *Agrobacterium*-mediated transformation.

19. The method of claim 17, wherein the mushroom cell or tissue is a protoplast, a spore, vegetative mycelium, or fruit body tissue.

20. A method for reducing or inhibiting one or more symptoms of a disease or disorder associated with vitamin A deficiency (VAD) in a subject comprising ingesting all or part of one or more mushrooms of claim 1.

21. The method of claim 20, wherein all or a part of the fruiting body of the mushroom is ingested.

22. The method of claim 20, wherein the one or more symptoms of a disease or disorder associated with vitamin A deficiency (VAD) are selected from the group consisting of blindness, abnormal visual adaptation to darkness (nyctalopia), dry skin, dry hair, broken fingernails, impairment of the humoral and cell-mediated immune system, bitot spots, pruritus, keratomalacia, xerophthalmia, corneal perforation, follicular hyperkeratosis (phrynoderma), excessive deposition of periosteal bone, anemia, and keratinization of mucous membranes.

23. The method of claim 20, wherein the one or more mushrooms comprise an effective amount of provitamin A to provide at least about 400; 500; 600; 700; 800; 900; 1,000; 1,100; or 1,200 retinol activity equivalents (RAE) to the subject.

24. The method of claim 20, wherein the mushrooms contain at least about 1, 2, 3, 4, 5, 10, 15, 20, 25, 30, 35, 40, 45, 50 µg or more of provitamin A per gram dry weight of mushroom.

25. The transgenic mushroom according to claim 6, wherein the transgenic mushroom comprises [The method of claim 21, wherein the mushrooms contain] at least about 1, 2, 3, 4, 5, 10, 15, 20, 25, 30, 35, 40, 45, 50 µg or more of provitamin A per gram dry weight of mushroom.

* * * * *